United States Patent [19]

Pettersson et al.

[11] 4,110,044
[45] Aug. 29, 1978

[54] METHOD FOR DETERMINATION OF CONCENTRATION

[75] Inventors: Torulf Pettersson, Stockholm; Gerdt Fladda, Täby; Lennart Eriksson, Vallentuna, all of Sweden

[73] Assignee: Svenska Traforskningsinstitutet, Stockholm, Sweden

[21] Appl. No.: 744,362

[22] Filed: Nov. 23, 1976

[30] Foreign Application Priority Data

Dec. 1, 1975 [SE] Sweden ............................ 7513524

[51] Int. Cl.² .................. G01N 21/26; G01N 33/46
[52] U.S. Cl. ............................ 356/103; 250/564; 250/574; 356/208
[58] Field of Search ............ 356/102, 103, 104, 208; 250/564, 573, 574

[56] References Cited

U.S. PATENT DOCUMENTS

| 3,724,957 | 4/1973 | Tamate et al. | 356/208 |
| 3,858,851 | 1/1975 | Ogle | 356/208 |
| 3,879,129 | 4/1975 | Inoue | 356/208 |

*Primary Examiner*—John K. Corbin
*Assistant Examiner*—R. A. Rosenberger
*Attorney, Agent, or Firm*—Pollock, Vande Sande and Priddy

[57] ABSTRACT

The percentage of suspended substances in a flowing medium is indicated by illuminating said medium with light perpendicularly to the direction of flow. The light intensity is held mainly constant at a predetermined value. Detection is made by a first light detector of light radiated from the medium in a predetermined direction and the electrical signal obtained is led to a device squaring the effective value of the portion of said signal lying within a predetermined frequency range. The percentage of the suspended substance is obtained from said square of the effective value.

12 Claims, 6 Drawing Figures

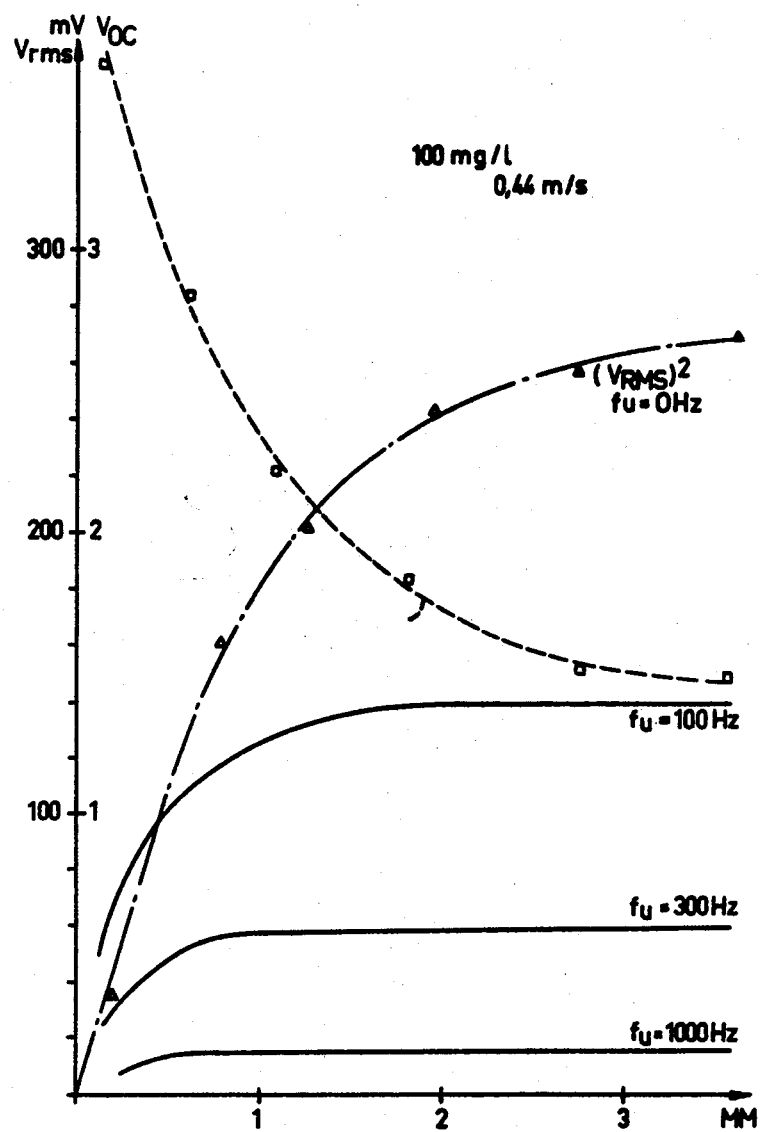

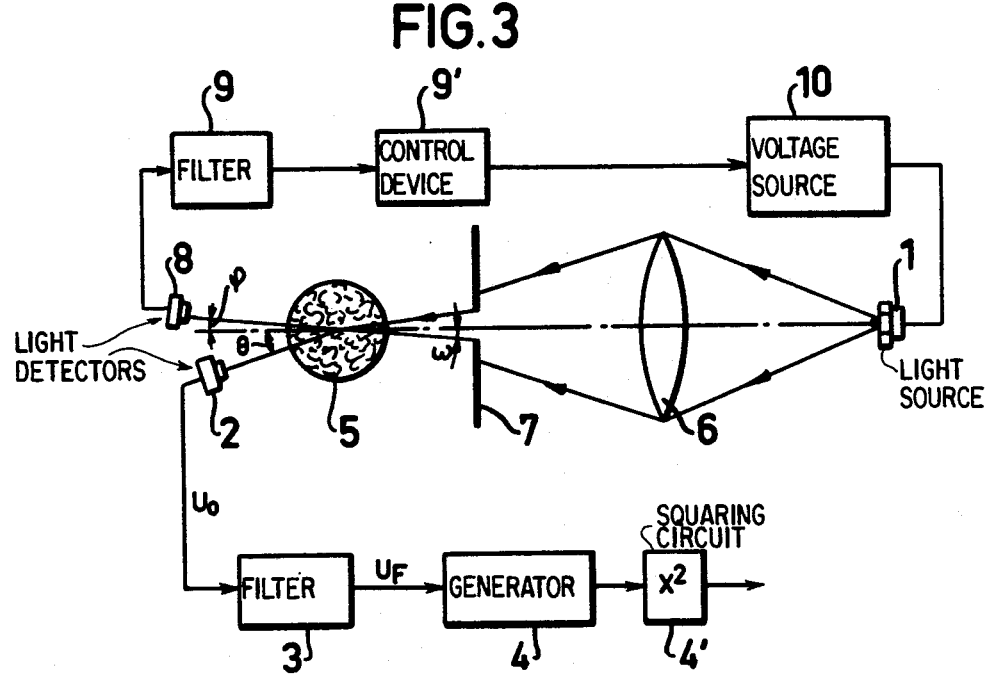
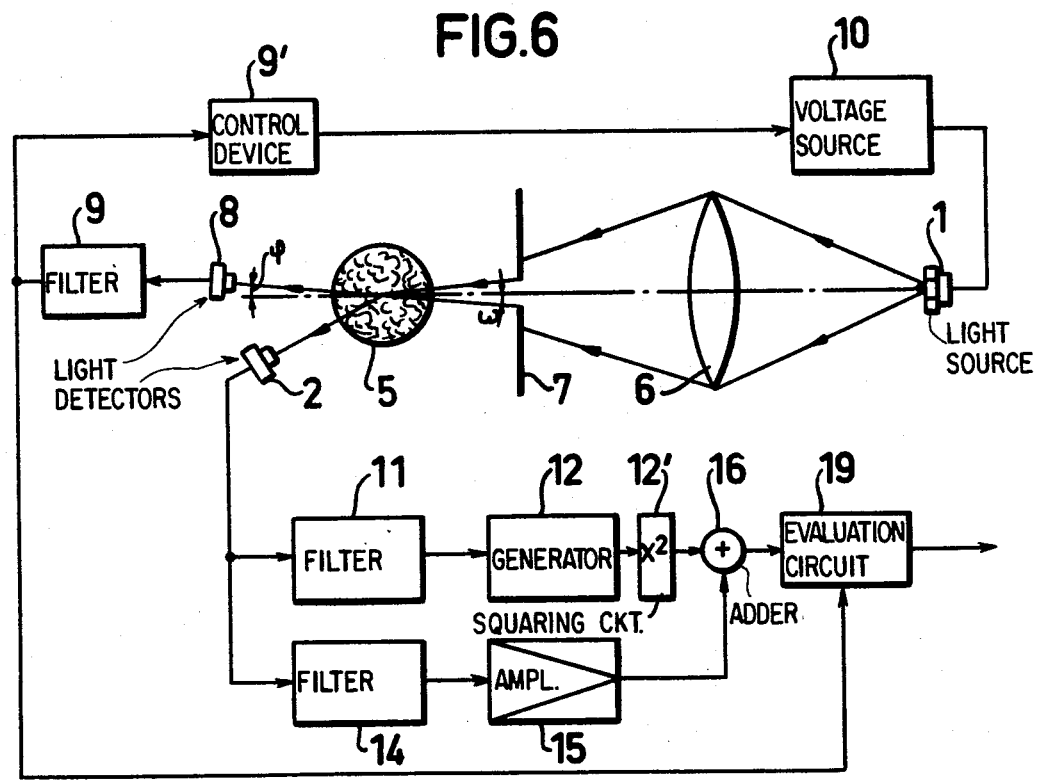

METHOD FOR DETERMINATION OF CONCENTRATION

The present invention relates to a method for indicating the content of suspended substances, existing is a flowing medium.

Especially in forest industry it is of a great interest to be able to measure the percentage of suspended substances, in the first place fibres and fibre fragments in various wastewaters. In nowadays used standard methods suspended substances mean such material that may be removed mechanically by filtration. Such suspended substances may consist of many different components, primarily fibre material, and different filling agents from paper manufacture possibly being of very varying size.

The instruments now available for measuring suspended substances, such as turbidity meters, being based on the general light scattering ability of the sample, or measuring devices operating with polarized light, permit determination of the percentage of suspended substances, provided that variations in composition do not exist. Typical for the waste discharge from forest industry is, however, that such variations exist, especially in so-called occasional waste discharges due to disturbances or errors in the manufacturing process.

Turbidity measuring instruments are often much more sensitive to discharges from fine fractionation (for instance fibre fragments) than for discharges of first-rate fibres, and, therefore, an increase in the output signal from an instrument of said type may indicate a large waste discharge of first-rate fibres or also a considerably smaller discharge from fine fractionation.

Since fibres have a great value, it is of interest to try to be able to re-use the fibres in wastewater in the production. Said fibres can, if they leave the external waste treatment plant of the factory, owing to their size gather in fibre bars near the waste outlet, in contrast to fine fractionation, that can be kept suspended in water for a long time, possibly causing environmental disturbances of other kinds. An increased number of first-rate fibres in wastewater is often an indication that something in the system has got out of order and must be corrected. Therefore, it is often desirable to be able to selectively measure the quantity of first-rate fibres in wastewater, and there is also an instrument on the market, which substantially only responds to the quantity of first-rate fibres in wastewater, but for which the quantity of fine fractionation does not give a noticable indication.

Existing guide-lines for the control of activity dangerous to the environment in forest industry state that the percentage of suspended substances, delivered by a factory to a receiving body, must be measured and reported to the authorities. The increased requirements as to control have also emphasized the need of an automatic, possibly continuously recording instrument, which can discover rapid variations of the percentage value.

Up to now measurements of suspended substances in forest industry have in most cases taken place in the laboratories of the factory by means of mechanical separation of a sample, which has usually been obtained by means of an automatic sampler which, at regular intervals, collects partial samples into a collecting sample (in most cases a 24 hours sample). Said method is slow and comparatively expensive, since it requires manual handling, and gives different results for different compositions of sample. The advantage of said method is, that it functions and is simple. The accuracy is satisfactory, but care is required for its maintenance. The method is, however, only convenient for sample test control.

It is true that there is also an already known method where a light source illuminates a suspension and where the light passing through the liquid in a certain direction is detected. According to said method the direct voltage level of the signal is measured and, furthermore, the number of times is counted in which the voltage exceeds a preset threshold level during a fixed time. Said method in itself operates in a satisfactory way, but certain calibration difficulties exist, since the accuracy of measurement is dependent on both the preset threshhold value and on different coefficients, with which the various indicated values must match. Said apparatus also gives a measuring value which is dependent on the flow velocity of the liquid.

The object of the present invention is to obtain a method by which the total percentage of suspended substances is accurately achieved, independent on the particle size distribution, and by which the advantages of the various methods described above are combined while obviating the weakness of said methods in measuring the total percentage of suspended substances. The method according to the invention, in addition to producing an indication of the total percentage of suspended substances, also makes it possible to state a measure of the particle size distribution. The method of the invention gives a possibility of a more continous control of the variation in time of various components, enabling an early tracing of changes.

Naturally, the method of the invention is not only suitable for use in forest industry, but it is also applicable in many other connections, where it is desirable to find out the percentage of suspended substances in a liquid. This especially applies to situations where fractions of different size appear in the liquid, which is often the case.

The invention will be better understood by reference to the accompanying drawings, in which FIG. 1 is a diagram which illustrates for short fibres and for long fibres, detected light intensity transformed into voltage as a function of frequency;

FIG. 2 illustrates the squared effective value of the alternating voltage portion of the signal as a function of fibre length in the suspended substance for the whole alternating voltage portion and the effective value for the alternating voltage portion after the signal has first passed a highpass filter having three different limit frequencies and also illustrates the direct voltage level of the received signal relative to a fixed level as a function of the average fibre length in the suspension;

FIG. 3 illustrates a first embodiment of a device for carrying out the method of the invention;

FIGS. 5 and 6 illustrate two other different embodiments of devices for carrying out the mthod of the invention.

Figure 1:
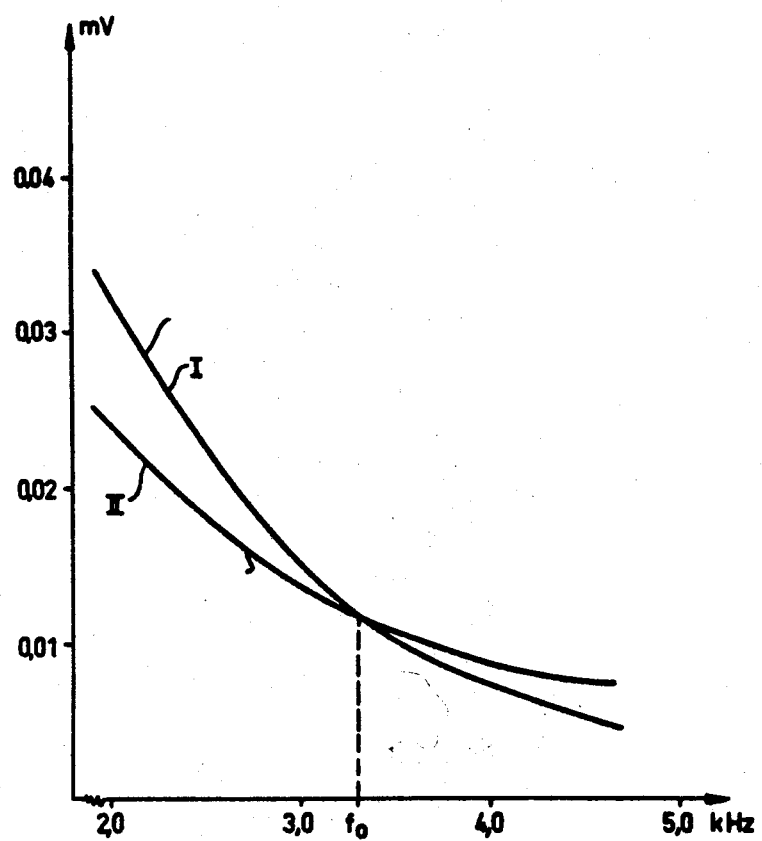

The method of the invention is based on the fact, that in a suspension of a fibre material in fine fraction, i.e. fibres with a short fibre length, the fibre material is more evenly distributed throughout a liquid volume than if the liquid contains a coarse fraction of fibre material, i.e. fibres with a long fibre length. The liquid will for the same percentage of fibre material be more turbid if it contains a fine fraction than if it contains a coarse fraction. This implies that if a flowing liquid containing a suspension is illuminated with light approximatively perpendicularly to the direction of flow, and said light is focused in the liquid with a solid angle ω and if the radiation passing through the liquid on the other side is detected either in the elongation of the direction of incidence or at a certain angle in relation to said direction, it is possible to obtain, if the intensity of the detected light is transformed into an electrical signal, for the same percentage of suspension with a coarse fraction, a signal with strong variations with a relatively low frequency and with a relatively small difference in direct current value compared with a signal without any suspension in water, and with a fine fraction, a signal, with high frequency variations and with a relatively large direct current component. That this is really the case can be easily realized, if first a suspension with a coarse fraction is regarded, where evey fibre passing the light flow gives rise to a distinct change in the received signal of a relatively large duration, obtained whether a fibre stands in the way of the light beam from the light source for the detector, or reflects light towards the detector. The more sparsely the the fibres are distributed in the suspension, the greater is the chance that each fibre passing the beam between the light source and the detector will give rise to a single signal change, and that two fibres do not give rise to signal changes simultaneously, thus resulting in a pulse formed received signal. The more fibres that simultaneously appear in the part of the liquid just passing the beam between the light source and the detector, the greater is the probability that more fibres simultaneously influence the light towards the detector, bringing about that the signal will vary more complexly with a larger number of frequency components but still with a predominance of low frequencies.

If, on the other hand, the fibres of the coarse fraction are ground into smaller particles, it is easily understood that each fibre part in the suspension so obtained when passing the beam between the light source and the detector will give rise to a relatively short pulse, but that a larger number of fibre parts will pass after each other and beside each other, so that even a low percentage will give a relatively "turbid" signal with a strongly varying frequency content and with a certain predominance of higher frequencies compared with the coarse fraction and with a relatively large direct voltage component.

In FIG. 1 two curves are shown of the detected light transformed into voltage as a function of frequency, but with the omission of the direct voltage component, for two different suspensions with a predetermined percentage of suspended substances. Curve I refers to the frequency variation for long fibres and curve II for short fibres. Naturally, the frequencies are directly dependent on the velocity of the flow of the liquid. As is apparent from the diagram the curves are intersecting at the frequency $f_0$. Curve I for long fibres shows a higher voltage within the low frequency range of frequencies and a lower voltage within the high frequency range than curve II. For higher percentages than that shown by the curves, these will be displaced approximatively parallelly in an upward direction, and the intersections will approximatively lie above each other, however, with a certain displacement to the right, since the alternating voltage component as such will decrease faster for a fine fraction than for a coarse fraction, while, on the other hand, the direct voltage component will increase faster for a fine fraction than for a coarse fraction, owing to the above described increased turbidity of the suspension for higher percentages. However, it is possible to find a frequency range around the intersection point, which the effective value of the voltage, i.e.

$$\sqrt{\frac{1}{T} \int_O^T u^2 dt}$$

is identical for both curves, and that said relationship with the same limit frequencies will also be applicable with a good approximation for other percentages the one illustrated in FIG. 1 within a limited percentage range.

As is apparent from FIG. 1 much greater difference is obtained between curve I and curve II for low frequencies than for high frequencies. In consequence thereof it is possible to select the chosen frequency range in such a way that a low-frequency part of the total frequency band is cut off.

This result is not quite true for very short fibres, but for the indication of the percentage of a suspension having a fraction above a predetermined coarseness, the same value will be obtained for the effective value of detected light transformed to voltage. This is readily apparent from FIG. 2 in which the solid curves show the effective value of the alternating voltage portion of the signal obtained from the above-mentioned detector after passage through a highpass filter with different limit frequencies as a function of the fibre length in a suspension.

These curves are obtained for different suspensions with a fibre percentage of 100 milligrams per litre with fibres of different lengths, by measuring the effective value of the alternating voltage portion of the output signal of the detector after the passage through different highpass filters. As is apparent from the different curves, an almost horizontal curve is obtained above a predetermined fibre length. The horizontal part of the curve will be more extended to the left for shorter fibres, the higher the limit frequency is selected, but the voltage value obtained will simultaneously be strongly decreased for higher selected limit frequencies. As is apparent from a comparison with FIG. 1, the largest differences between the curves I and II appear at the leftmost part of the curves, where the limitation is made.

The consequence thereof is that a fairly good approximation can be obtained when measuring the fiber percentage in a suspension where the fibre content can be expected to contain fibres which are mainly above a definite length, by means of a highpass filter after the above mentioned detector.

FIG. 2 also shows on an enlarged scale the direct voltage portion of the signal delivered from a detector placed in the angular position 0°, i.e. just opposite the light source on the other side of the focusing point, said signal being deducted from a direct voltage value obtained for clear water as shown by a dashed line. As is apparent from the diagram, the direct voltage signal is largest for fine fractionation, i.e. for short fibres, and then decreases for coarse fractionation, i.e. for long fibres, being fully in correspondence with the above discussion. On a comparison between the curve for the direct voltage signal and that for the squared effective value over the whole alternating voltage portion there is left no room for doubt, that the curve for the direct voltage signal and that of the unfiltered alternating voltage signal run in opposite directions, and investigations have shown, that if the above mentioned direct voltage difference signal multiplied by an appropriate factor is added to the mean value of the squared alternating voltage portion, a curve is obtained that is practically horizontal for all fibre lengths. For different fibre percentages said curve is parallelly displaced upwards for higher percentages of suspended material and downwards for lower percentages. If the square of the effective value of the alternating voltage part is added to the direct voltage signal multiplied by the appropriate factor, the result will be fully independent of the flow velocity of the liquid down to very small velocities, which is a property of a great value making this embodiment of the method very useful.

From the curves for the direct voltage difference signal and that of the unfiltered alternating voltage signal it is also apparent that for instance by dividing said signals it is possible to obtain a signal with strong variation for different fractions which may be used for indicating a change in the relation between coarse fraction and fine fraction in the suspension being investigated.

Figure 5:
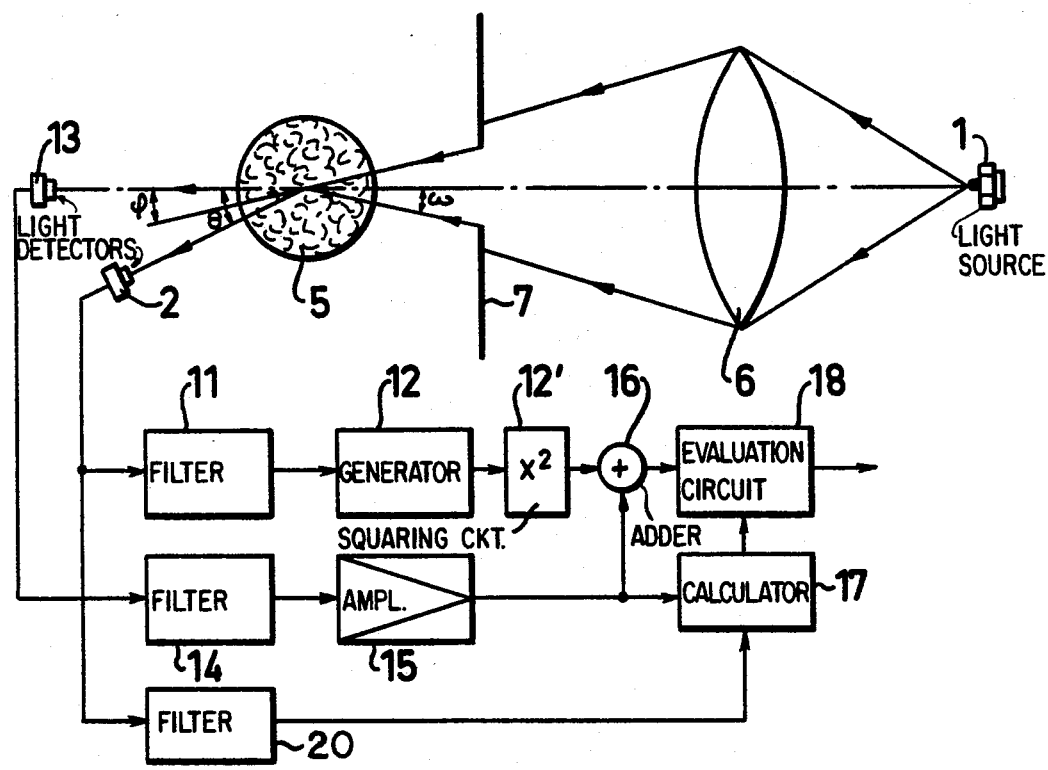

FIGS. 3, 5 and 6 show three different embodiments of devices for carrying out different embodiments of the method according to the invention. In the device shown in FIG. 3 a light source 1, via an optical element 6 and a diaphragm 7 illuminates a transparent tube 5, through which a liquid containing suspended substance is flowing. On the other side of the tube at an angle $\theta$ to a line from the light source 1 through the centre of the tube a light detector 2 is placed. The angle $\theta$ is, if only the alternating voltage part of the signal from the detector is to be indicated, in no way critical, but may be selected between 0° and 90°. The magnitude of the signal is, however, influenced thereby. The light intensity detected by the light detector 2 is transformed into an electric voltage signal, which is fed through a filter 3 to a generator 4 of effective value. This generator 4 can be a voltmeter, indicating the true effective value (true RMS-voltmeter), the suspension percentage, however, not being linear with respect to the scale of the voltmeter. A linear relation to the suspension percentage, at least for low values thereof may, however, be obtained if the output signal from said generator 4 is squared in a squaring circuit 4' connected in the signal direction after said generator.

If a measurement of the fibre percentage for fine fraction is desired, the filter 3 is a bandpass filter, with its limit frequencies suitably selected on each side of the frequency $F_0$ in FIG. 1. This will give a direct dependence between the velocity of flow of the liquid and the frequency, and therefore a control of one of said magnitudes relative to the other one must be made.

If it is less important to be able to indicate the content of a very fine fractioned suspension, the filter 3 is instead a highpass filter, where the lower limit frequency, as is evident from FIG. 2, is higher the more fine fractioned suspension is to be indicated. The advantage of this embodiment is that the dependence on the velocity of flow of the liquid will not be critical. However, it should be observed that the lower limit frequency of the filter is dependent on the velocity of flow, and therefore instead of raising the limit frequency it is possible to decrease the velocity of flow, and to get the same curves as in FIG. 2. The measuring time, however, must be in proportion to the velocity of flow in order that the same scatter of measuring data should be obtained.

Sometimes colour variations can occur in the liquid, flowing through the transparent tube, and such variations must be compensated. Therefore, in the device according to FIG. 3 a second light detector 8 is shown, which is placed (at a definite) angle $\phi$ to the line through the light source and the center of the tube.

If light with a definite solid angle $\omega$ is to incide in and is to be focused in a liquid without content of light scattering particles, the light radiating from the liquid is in principle evenly distributed over the same solid angle as the inciding light on the other side of the focusing point, so that a light detector, which is moved around the focusing point would not be able to detect any light outside the solid angle range. Within said range an even light flow would then be obtained, provided that the inciding light flow is evenly distributed over the solid angle range of the inciding light. A light detector which is moved around the focusing point opposite the inciding light should thus give a rectangular output pulse. This can never be obtained in practice, since the light scattering phenomena always appear, by an output signal from a detector, being moved around the focusing point, will be Gauss-curve-shaped or bellshaped with the strongest signal opposite the light source and with steep flanks when passing the range around the limit of the solid angle range. The more light scattering particles the liquid contains, the lower is the signal which is obtained opposite the light source, and the flatter are the flanks of the Gauss-curve (see FIG. 4). At the same light absorption in the liquid but with different scattering, however, the obtained Gauss-curves always have the same intersection points K, which has been proved when measuring conifer wood sulphate of fractions > 16; 16–30; 30–50; 50–100; 100–200; < 200 Mesh for concentrations up to 200 mg/l. If a light detector is placed in a direction relative to the focusing point such that the Gauss-curves run through the same point, the signal indicated by said detector will be independent of the scattering phenomena and thus only dependent on the absorption of the liquid of the light used, i.e. the colour variation of the liquid. It should be observed that this applies to the direct voltage portion of the signal only, so that consequently in said point, when measuring a flowing liquid, a signal will be obtained which will fluctuate around a constant value.

If an increase in the absorption in the liquid occurs, the two curves will fall in relation to the increased absorption, and consequently also the value in the point K at the angle position $\phi$. This is utilized for colour compensation, by placing the light detector 8 in the angle position $\phi$ and by feeding the voltage signal emitted from said detector through a filter 9, that filters out the alternating voltage portion, to a control device 9' which in turn controls the drive voltage source 10 of the light source 1 so that the direct current component fed from the detector 8 will remain constant. Any other type of colour compensation may of course be used.

Since the placement of the detector 2 is not critical, the detector 2 and the detector 8 in said embodiment can be one and the same placed in the angle position $\phi$, the output signal from said detector in this case being divided into a direct current portion for colour compensation and into an alternating voltage portion for measuring the suspension percentage.

The device shown in FIG. 5 utilizes the fact that it is possible to obtain a practically horizontal curve for all types of fractions if the squared effective value of the alternating voltage portion of the signal from the detector 2 is added to the difference between two direct voltage signals from a light detector multiplied by a constant.

Figure 4:
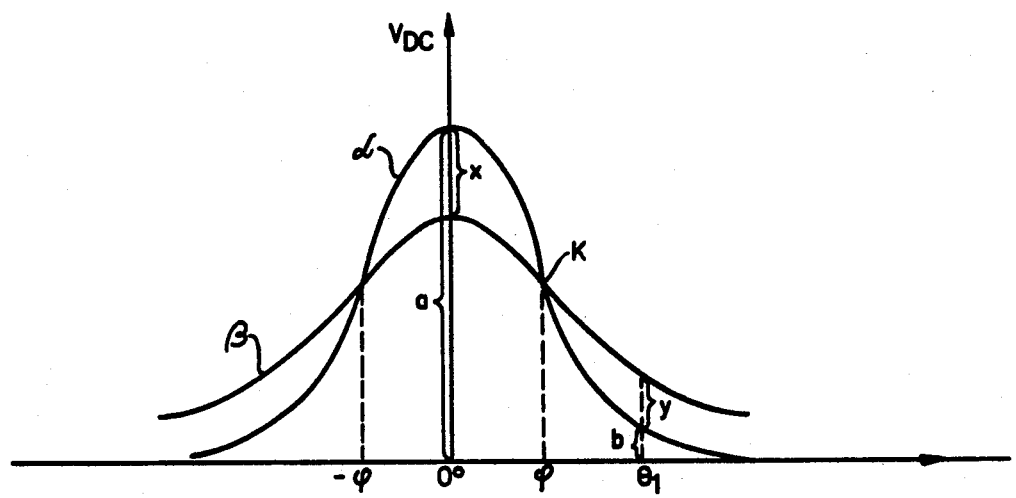
FIG. 4 illustrates the shape of a curve used for explaining a part of the invention.

If in FIG. 4 curve α relates to clear water, i.e. to water without any content of suspended substance and curve β relates to water with suspended substance, it is apparent that the difference between the output voltage level for a detector placed at the angle position 0° is $x$, and for a detector, placed at the angle position $\theta$, is $y$. Trials have shown that the proportion between $y$ and $x$ is approximatively a constant for the low percentages of the suspension, for which the method of the invention is suitable. Therefore, the direct voltage portion with reference to a constant value can be used from a detector, which can be placed in any angle position except just in the angle position $\phi$. The angle position $\theta$ should, however, lie on an easily definable part of the curve for clear water, different from zero.

In FIG. 5 a detector 13 is placed in the angle position 0°. The output signal therefrom is fed to a filter 14, in which the alternating voltage portion is filtered out. The output signal of the filter 14 is fed to an amplifier 15, the amplification of which is adapted to the constant with which the direct voltage signal is to be multiplied, and can consequently have an amplification below 1. As in FIG. 3 the output signal is fed from the light detector 2 to a filter 11. However, in this case said filter filters out the direct current part only of the signal. Thereafter the effective value of the signal is produced or generated in the effective value generating device 12 and is squared in the squaring circuit 12'. The signal from the element 12' and the signal from the amplifier 15 are added in the adder 16.

Also in said embodiment a colour compensation is made, but instead this takes place at the output signal. If the colour increases in the liquid, i.e. for increasing absorption, the two curves are lowered in FIG. 4 and the lowering of the curves at the angle position 0° and at the angle position $\theta$ will have a certain relation to each other. This is utilized in such a manner that the signal from the detector 2, which in this embodiment is placed in the angle position $\theta$, separated from $\phi$, is fed to an additional filter 20 filtering out the alternating voltage portion of the signal. The signals from the filter 20 and from the amplifier 15 or alternatively directly from the filter 14 are each one fed to an individual input of a signal treating device 17 calculating the given relation between the signals, and in dependence thereon a signal is fed to a control input of an evaluation circuit 18, the output signal obtained from the adder 16 being thus colour compensated. Instead of using the signals from the detectors 2 and 13, a detector 8 can, of course, also in this case be placed in the angle position $\phi$, and its output signal can be fed to the control input of the evaluation circuit 18 for the colour control.

As is apparent from the above statements, the detectors 2 and 13 can of course for the measuring of the suspension percentage be one and the same detector, the output signal of which is divided into a direct voltage portion and an alternating voltage portion and is treated individually in the circuits 11, 12, 12', 14 and 15, and this is also shown in FIG. 6. In accordance with said Figure the colour compensation takes place exactly as in FIG. 3 with a detector 8 placed in the angle position $\phi$. In said embodiment also the output signal from the filter can be fed to the control input of an evaluation circuit 19.

Many different modifications are possible within the scope of the invention. The transparent tube, for instance, must not have a circular section but may be of a square type if a compensation of the light beam is performed. It is also possible not to have any tube at all, but to lower the light source with the optical elements and the detectors in the liquid proper. Of course, the method according to the invention is not only applicable for measuring a flowing liquid but also for measuring particles existing in a flowing gas.

What is claimed is:

1. A method for indicating the percentage of suspended substances in a flowing medium, said medium being illuminated with light perpendicularly to the direction of flow with an intensity that is mainly constant and predetermined during measuring, the light radiated from the medium in a predetermined direction being detected by a first light detector transforming the detected light into an electrical signal varying in dependence on the light intensity, characterized in forming the square of the effective value of that portion of the signal which is within a predetermined frequency range, and deriving the percentage by means of said square of the effective value.

2. A method according to claim 1, characterized in that the limit frequencies of the frequency range are placed on each side of the point of intersection for two curves of the signal voltage as a function of the frequency, one of said curves being plotted for large particles and the other one for small particles, said limit frequencies being so selected that the square of the effective value of the signal lying between the limit frequencies is the same for coarse separation as for fine separation.

3. A method according to claim 1, characterized in that the frequency range only comprises frequencies above a predetermined lower limit frequency.

4. A method according to claim 1, characterized in forming the square of the effective value of the signal for the whole alternating voltage portion, and detecting in a second light detector the light radiated from the flowing medium in a predetermined direction and transforming said light into an electrical signal, the direct voltage component of which is determined in relation to a direct voltage component obtained from said detector in the same direction for flowing medium without suspended substances, for forming together with said square of the effective value a signal which is indicative of the percentage of the suspended substances.

5. A method according to claim 4, characterized in summing the square of the effective value and the direct voltage component, multiplied by a constant.

6. A method according to claim 4, characterized in dividing the square of the effective value and the direct voltage component by each other, the result obtained giving a measure of the separation distribution in said medium.

7. Method according to claim 6, characterized in that the output signal from a third light detector, multiplied by a definite constant, is brought together with the signal from the first light detector, and, where appropriate, from the second light detector, to form a signal representing the percentage of suspended substances.

8. Method according to claim 4, characterized in that the first and the second light detector are one and the same detector, the output signal of which is divided into an alternating voltage portion and a direct voltage portion.

9. Method according to claim 4, characterized in that a third light detector responsive to light radiating from the flowing medium is provided to control the illumination of said medium, the second light detector being placed in an angle position which is separated from the angle position in which the third light detector is placed.

10. A method according to claim 1, characterized in feeding a direct voltage component, from a further light detector which transforms into voltage light radiated from the flowing medium in a direction so chosen in dependence on the solid angle of the incident light that variations in said direct voltage component are only dependent on the light absorption in said medium, to a control device for controlling the illumination of said medium in such a way that the direct voltage component of the output signal from said further light detector is kept at a constant or a controlled value.

11. Method according to claim 10, characterized in that the first and the further light detector are one and the same detector, the output signal of which is divided into an alternating voltage portion for indicating the suspension percentage and a direct voltage portion for colour compensation.

12. A method according to claim 1 characterized in letting the direct voltage components from two light detectors which transform into voltages light radiated from the flowing medium in two directions chosen to be each on one side of a direction which in dependence on the solid angle angle of the incident light is so chosen that variations in a direct voltage component detected in said direction are only dependent on the light absorption in said medium, cooperate to form a signal which is dependent on the light absorption in the medium, said signal being fed to a control device for controlling the illumination of said medium in such a way that the said signal is kept at a constant or a controlled value.

* * * * *